US00PP30237P2

(12) United States Plant Patent
Eveleens

(10) Patent No.: US PP30,237 P2
(45) Date of Patent: Feb. 26, 2019

(54) ***HYDRANGEA* PLANT NAMED 'HORTMABLUEBEL'**

(50) Latin Name: *Hydrangea macrophylla*
Varietal Denomination: Hortmabluebel

(71) Applicants: KOLSTER HOLDING B.V., Boskoop (NL); HORTEVE BREEDING B.V., Aalsmeer (NL)

(72) Inventor: Cornelis P. Eveleens, Aalsmeer (NL)

(73) Assignees: Kolster Holding B.V., Boskoop (NL); Horteve Breeding B.V., Alsmeer (NL)

( * ) Notice: Subject to any disclaimer, the term of this patent is extended or adjusted under 35 U.S.C. 154(b) by 0 days.

(21) Appl. No.: 15/731,888

(22) Filed: Aug. 21, 2017

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

(56) References Cited

PUBLICATIONS

UPOV hit on *Hydrangea* plant named 'Hortmabluebel', QZ PBR 20163227, filed Dec. 20, 2016.*
EU PBR application, Feb. 15, 2017, Horteve Breeding B.V.

* cited by examiner

*Primary Examiner* — Anne Marie Grunberg
(74) *Attorney, Agent, or Firm* — C. A. Whealy

(57) ABSTRACT

A new and distinct cultivar of *Hydrangea* plant named 'Hortmabluebel', characterized by its upright to broadly spreading plant habit; moderately vigorous to vigorous growth habit and moderate to rapid growth rate; freely branching habit with strong and thick sturdy stems; mophead-type inflorescences with large red purple-colored sterile flowers that can be easily "blued"; and good postproduction longevity.

3 Drawing Sheets

Botanical designation: *Hydrangea macrophylla.*
Cultivar denomination: 'HORTMABLUEBEL'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hortmabluebel'.

The new *Hydrangea* plant is a product of a planned breeding program conducted by the Inventor in Boskoop, The Netherlands. The objective of the breeding program was to create new *Hydrangea* plants with large inflorescences with numerous sterile flowers that can be easily "blued" and good postproduction longevity.

The new *Hydrangea* plant originated from a cross-pollination made by the Inventor in 2007 in Boskoop, The Netherlands, of *Hydrangea macrophylla* 'Love You Kiss', not patented, as the female, or seed, parent with *Hydrangea macrophylla* 'Renate Steiniger', not patented, as the male, or pollen, parent. The new *Hydrangea* plant was discovered and selected by the Inventor as a single flowering plant from within the progeny of the stated cross-pollination in a controlled greenhouse environment in Boskoop, The Netherlands in 2011.

Asexual reproduction of the new *Hydrangea* plant by vegetative terminal cuttings in a controlled environment in Boskoop, The Netherlands has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hortmabluebel'. These characteristics in combination distinguish 'Hortmabluebel' as a new and distinct *Hydrangea* plant:

1. Upright to broadly spreading plant habit.
2. Moderately vigorous to vigorous growth habit and moderate to rapid growth rate.
3. Freely branching habit with strong and thick sturdy stems.
4. Mophead-type inflorescences with large red purple-colored sterile flowers that can be easily "blued".
5. Good postproduction longevity.

Plants of the new *Hydrangea* can be compared to plants of the female parent, 'Love You Kiss'. Plants of the new *Hydrangea* differ primarily from plants of 'Love You Kiss' in inflorescence form as plants of 'Love You Kiss' have lacecap-type inflorescences. In addition, plants of the new *Hydrangea* and 'Love You Kiss' differ in sterile flower color as sterile flowers of plants of 'Love You Kiss' are white with pink-colored margins.

Plants of the new *Hydrangea* can be compared to plants of the male parent, 'Renate Steiniger'. Plants of the new *Hydrangea* differ primarily from plants of 'Renate Steiniger' in flowering habit as plants of the new *Hydrangea* are more freely flowering than plants of 'Renate Steiniger'. In addition, plants of the new *Hydrangea* have smaller sterile flower sepals than plants of 'Renate Steiniger'.

Plants of the new *Hydrangea* can be compared to plants of the *Hydrangea macrophylla* 'Hortmadace', disclosed in U.S. Plant Pat. No. 28,084. In side-by-side comparisons plants of the new *Hydrangea* differ primarily from plants of 'Hortmadace' in the following characteristics:

1. Plants of the new *Hydrangea* are taller than plants of 'Hortmadace'.
2. Plants of the new *Hydrangea* are more easily "blued" than plants of 'Hortmadace'.

Plants of the new *Hydrangea* can also be compared to plants of the *Hydrangea macrophylla* 'Kolmaru', disclosed in U.S. Plant Pat. No. 25,104. In side-by-side comparisons plants of the new *Hydrangea* differ primarily from plants of 'Kolmaru' in the following characteristics:

1. Plants of the new *Hydrangea* are taller than plants of 'Kolmaru'.
2. Plants of the new *Hydrangea* are more easily "blued" than plants of 'Kolmaru'.
3. Plants of the new *Hydrangea* and 'Kolmaru' differ in sterile flower color as plants of 'Kolmaru' have dark red-colored sterile flower sepals.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'Hortmabluebel'.

The photograph on the second sheet is a close-up view of a typical inflorescence of 'Hortmabluebel'.

The photograph on the third sheet is a close-up view of a typical inflorescence of 'Hortmabluebel' that has been "blued".

DETAILED BOTANICAL DESCRIPTION

Plants used in the aforementioned photographs and in the following description were grown during the late spring in 17-cm containers in a glass-covered greenhouse in Boskoop, The Netherlands and under cultural practices typical of commercial *Hydrangea* production. During the production of the plants, day temperatures ranged from 18° C. to 25° C. and night temperatures ranged from 16° C. to 17° C. Plants of the new *Hydrangea* were two years old when the photographs and description were taken. Plants of the new *Hydrangea* can be treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hortmabluebel'.

Parentage:

*Female, or seed, parent.*—*Hydrangea macrophylla* 'Love You Kiss', not patented.

*Male, or pollen, parent.*—*Hydrangea macrophylla* 'Renate Steiniger', not patented.

Propagation:

*Type cutting.*—By vegetative terminal cuttings.

*Time to initiate roots, summer.*—About three weeks at temperatures about 15° C. to 25° C.

*Time to produce a rooted young plant, summer.*—About six weeks at temperatures about 15° C. to 25° C.

*Root description.*—Medium in thickness, fibrous; typically creamy white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright and broadly spreading plant habit; overall plant shape is flattened globular; strong and sturdy lateral branches; moderate to rapid growth rate and moderately vigorous to vigorous growth habit.

*Plant height.*—About 59.5 cm.

*Plant diameter or area of spread.*—About 75.1 cm.

Lateral branch description:

*Branching habit.*—Freely branching habit; when pinched, about 14 lateral branches develop per plant.

*Length.*—About 40 cm.

*Diameter.*—About 8 mm.

*Internode length.*—About 8 cm.

*Texture.*—Smooth, glabrous; fully developed, woody.

*Aspect.*—Upright to about 35° from vertical.

*Strength.*—Strong, sturdy.

*Color.*—When developing: Close to 144A. Developed: Close to 144A; when woody, close to 199B and N199B.

*Lenticels.*—Density: Dense. Length: About 2 mm. Diameter: About 0.5 mm. Color: Close to N186C.

Leaf description:

*Arrangement.*—Opposite, simple.

*Length.*—About 13.4 cm.

*Width.*—About 10.6 cm.

*Shape.*—Broadly elliptic to broadly ovate and broadly obovate.

*Apex.*—Apiculate.

*Base.*—Short attenuate.

*Margin.*—Serrate.

*Texture, upper surface.*—Smooth to slightly rugose, glabrous.

*Texture, lower surface.*—Smooth to slightly rugose, surface mostly glabrous, however small tufts of short hairs present at vein axils.

*Venation pattern.*—Pinnate.

*Color.*—Developing leaves, upper surface: Close to between NN137A and 141A. Developing leaves, lower surface: Close to 146A. Fully expanded leaves, upper surface: Close to between NN137A and 139A; venation, close to 144A to 144B. Fully expanded leaves, lower surface: Close to 147B; venation, close to 144B.

*Petioles.*—Length: About 3 cm. Diameter: About 4 mm. Texture and luster, upper surface: Smooth, glabrous; moderately glossy. Texture and luster, lower surface: Smooth, glabrous; slightly glossy. Color, upper surface: Close to 144A. Color, lower surface: Close to 144B; towards the margins, close to 144A.

Flower description:

*Flower type and habit*.—Showy sterile flowers and small inconspicuous fertile flowers arranged on mophead-type terminal panicles; panicles globular and slightly flattened in shape; fertile flowers face mostly upright and sterile flowers face upright to outwardly and slightly drooping depending on their position in the inflorescence.

*Fragrance*.—None detected.

*Natural flowering season*.—Plants flower from late spring to late summer in The Netherlands.

*Flower longevity*.—Fertile flowers last about five days on the plant, fertile flowers not persistent; sterile flowers last about six weeks on the plant, sterile flowers persistent.

*Quantity of flowers*.—Freely flowering habit; about 40 fertile flowers per panicle and about 85 sterile flowers per panicle.

*Panicle height*.—About 14.4 cm.

*Panicle diameter*.—About 21.7 cm.

*Fertile flower buds*.—Length: About 4 mm. Diameter: About 3.5 mm. Shape: Obovate. Color: Close to 157A to 157B and tinged with close to 68C; towards the base, close to 144A.

*Sterile flower buds*.—Length: About 2 mm. Diameter: About 3 mm. Shape: Flattened globular. Color: Close to 157B.

*Fertile flower diameter*.—About 6 mm.

*Fertile flower depth* (*height*).—About 4 mm.

*Sterile flower diameter*.—About 6.1 cm.

*Sterile flower depth* (*height*).—About 2.3 cm.

*Petals, fertile flowers*.—Quantity and arrangement: Four or occasionally five in a single whorl. Length: About 4 mm. Width: About 2 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D tinged with close to 76A to 76B. When opening and fully opened, lower surface: Close to 76C to 76D.

*Petals, sterile flowers*.—Quantity and arrangement: Four or occasionally five in a single whorl. Length: About 4 mm. Width: About 2 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D tinged with close to 76A to 76B. When opening and fully opened, lower surface: Close to 76C to 76D.

*Sepals, fertile flowers*.—Quantity and arrangement: Five or occasionally six in a single whorl. Length: About 1 mm. Width: About 1 mm. Shape: Ovate. Apex: Acute. Base: Broadly cuneate. Margin: Entire. Texture and luster, upper and lower surfaces: Smooth, glabrous; matte. Color: When opening, upper and lower surfaces: Close to 145A; towards the base, close to 145B. Fully opened, upper and lower surfaces: Close to 145A; towards the base, close to 145B; color does not change with development.

*Sepals, sterile flowers*.—Quantity and arrangement: Four or occasionally five in a single whorl. Length: About 3 cm. Width: About 4 cm. Shape: Broadly reniform. Apex: Broadly acute. Base: Cuneate. Margin: Dentate to serrate. Texture and luster, upper and lower surfaces: Smooth, glabrous; matte. Color: When opening, upper surface: Close to 73B; towards the apex, close to 73A. When opening, lower surface: Close to 73C; towards the apex, close to 73B. Fully opened, upper surface: Close to 68A; color does not change with development. Fully opened, lower surface: Close to 70C; color does not change with development.

*Pedicels, fertile flowers*.—Length: About 2 mm. Diameter: About 1 mm. Strength: Moderately strong. Aspect: About 25° from vertical. Texture and luster: Moderately pubescent; matte. Color: Close to 179C.

*Pedicels, sterile flowers*.—Length: About 3.2 cm. Diameter: About 2 mm. Strength: Moderately strong. Aspect: About 45° from vertical. Texture and luster: Moderately pubescent; matte. Color: Close to 75A to 75B.

*Reproductive organs, fertile flowers*.—Stamens: Quantity per flower: About eight. Filament length: About 2 mm. Filament color: Close to N155A. Anther length: About 1 mm. Anther shape: Oblong. Anther color: Close to 155A. Pollen amount: Moderate. Pollen color: Close to 159D. Pistils: Pistil quantity per flower: About three. Pistil length: About 1 mm. Stigma shape: Club-shaped. Stigma color: Close to NN155A. Style length: About 0.5 mm. Style color: Close to 155D. Ovary color: Close to 145B tinged with close to 179D.

*Reproductive organs, sterile flowers*.—Stamens: Quantity per flower: About eight. Filament length: About 2 mm. Filament color: Close to N155A. Anther length: About 1 mm. Anther shape: Oblong. Anther color: Close to 155A. Pollen amount: Moderate. Pollen color: Close to 159D. Pistils: Pistil quantity per flower: About three. Pistil length: About 1 mm. Stigma shape: Club-shaped. Stigma color: Close to NN155A. Style length: About 0.5 mm. Style color: Close to 155D. Ovary color: Close to 157D.

*Seeds*.—Seed development has not been observed on plants of the new *Hydrangea* to date.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 to 9.

It is claimed:

1. A new and distinct *Hydrangea* plant named 'Hortmabluebel' as illustrated and described.

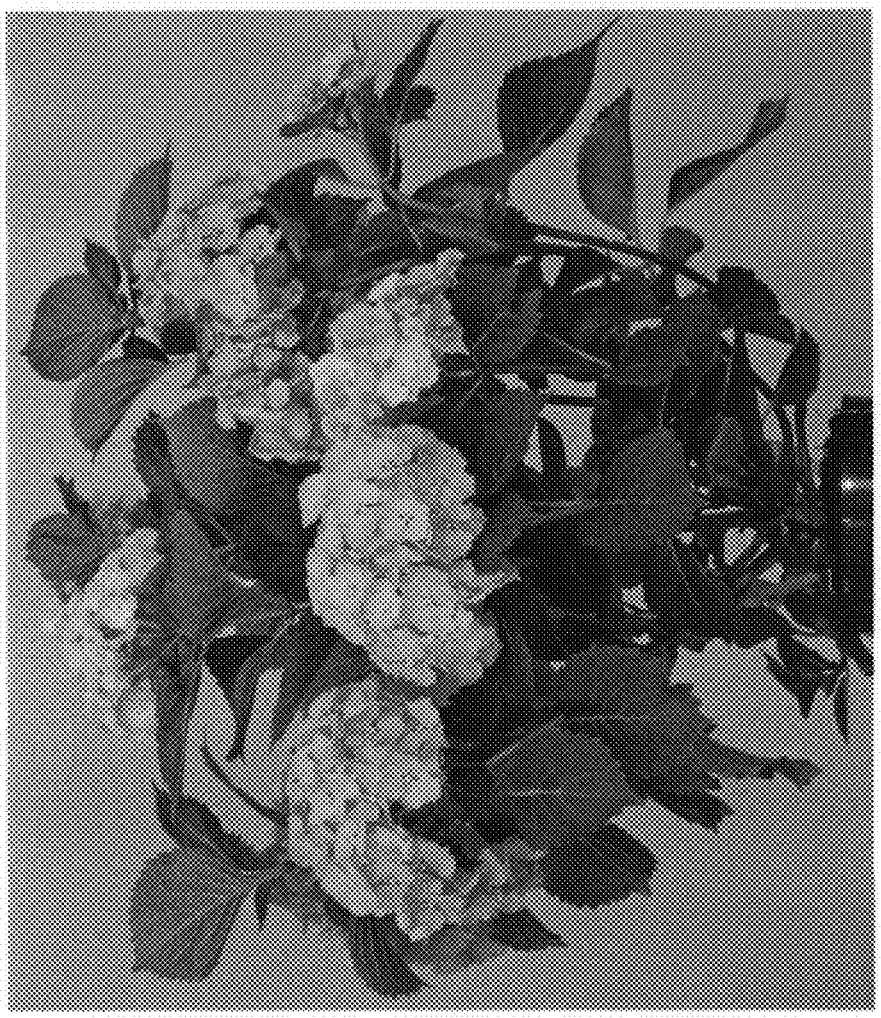

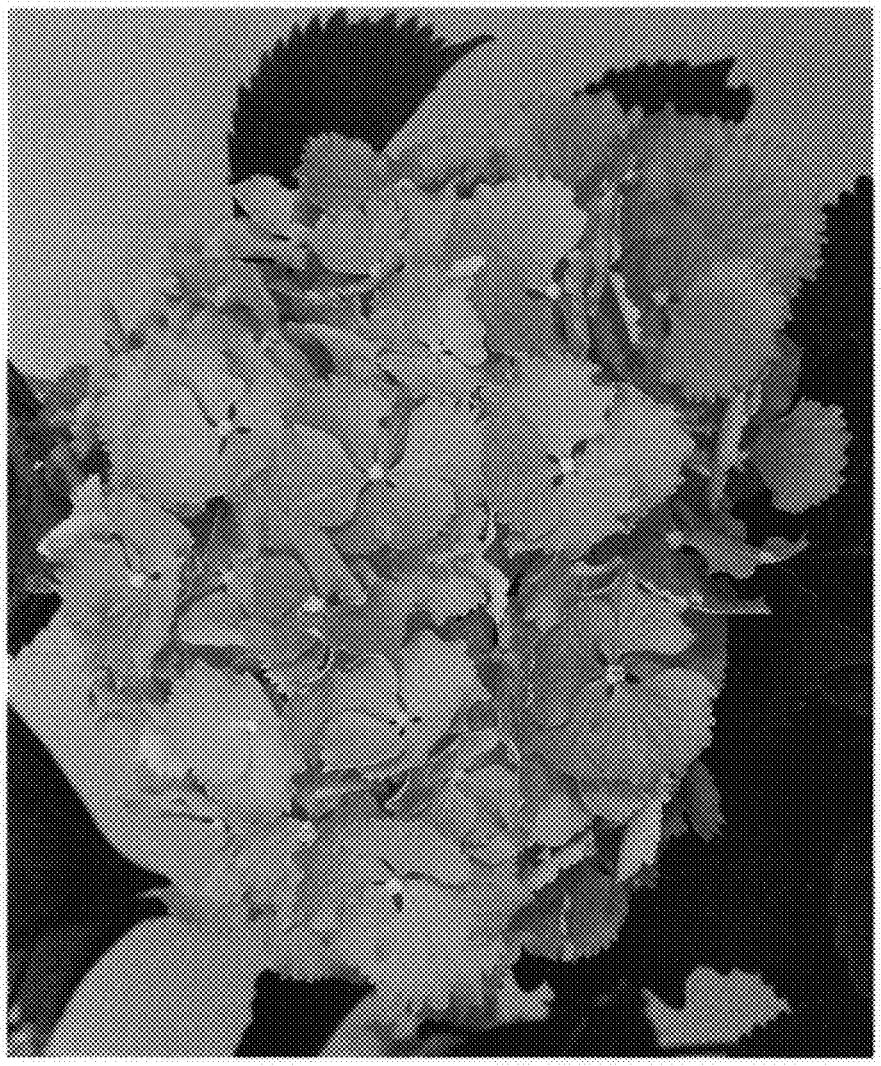

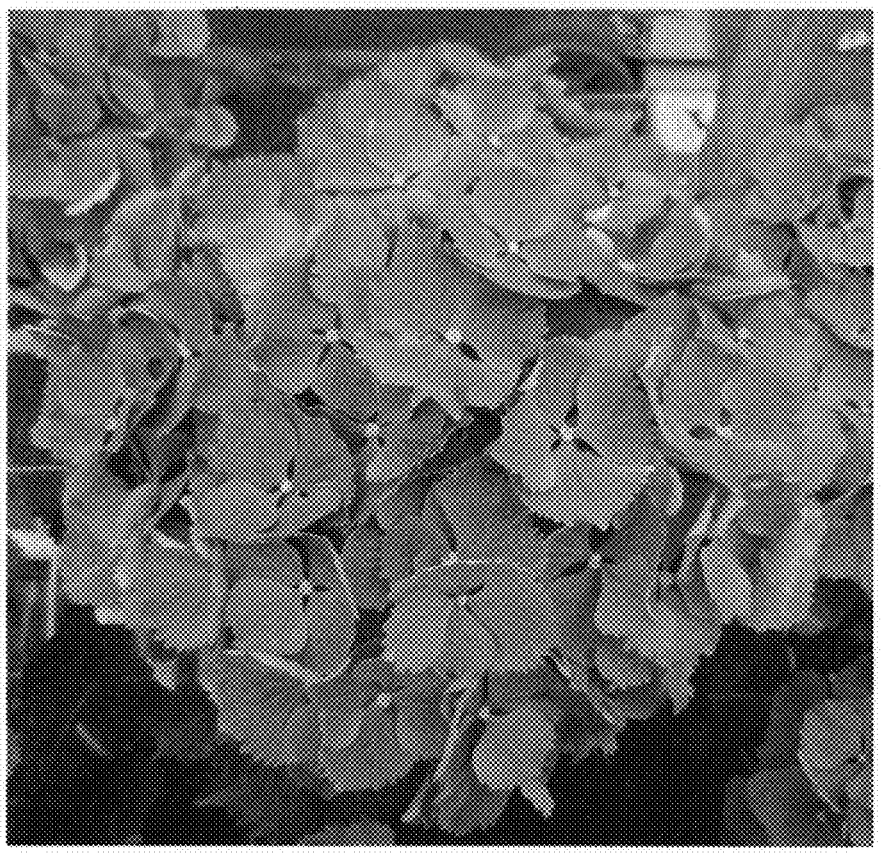

* * * * *